United States Patent
D'Ambrosio et al.

(10) Patent No.: US 8,979,913 B2
(45) Date of Patent: Mar. 17, 2015

(54) PROGRAMMABLE CIRCADIAN RHYTHM ADJUSTMENT

(75) Inventors: Carolyn Marie D'Ambrosio, Dover, MA (US); Nargues Amir Weir, Reston, VA (US); Blathnaid Kinch, Reston, VA (US)

(73) Assignee: The Complete Sleep Company LLC, Reston, VA (US)

( * ) Notice: Subject to any disclaimer, the term of this patent is extended or adjusted under 35 U.S.C. 154(b) by 0 days.

(21) Appl. No.: 13/115,019

(22) Filed: May 24, 2011

(65) Prior Publication Data

US 2012/0303099 A1 Nov. 29, 2012

(51) Int. Cl.
*A61N 5/06* (2006.01)

(52) U.S. Cl.
CPC ....... *A61N 5/0618* (2013.01); *A61N 2005/0662* (2013.01); *A61N 2005/0626* (2013.01)
USPC .................. 607/88; 607/89; 607/90; 607/91; 607/94

(58) Field of Classification Search
USPC .................................................... 607/88–94
See application file for complete search history.

(56) References Cited

U.S. PATENT DOCUMENTS

| | | | |
|---|---|---|---|
| 2006/0009822 A1* | 1/2006 | Savage et al. | 607/88 |
| 2009/0128044 A1* | 5/2009 | Nevins | 315/182 |
| 2010/0211137 A1* | 8/2010 | Kim et al. | 607/88 |

OTHER PUBLICATIONS

American College of Chest Physicians, ACCP Sleep Medicine Board Review 4th Edition, Jan. 2009, pp. 1-331, Northbook, IL.
Shirani et al., Illuminating Rationale and Uses for Light Therapy, Journal of Clinical Sleep Medicine, vol. 5, No. 2, May 2008, pp. 155-163.

\* cited by examiner

*Primary Examiner* — Lynsey Crandall
*Assistant Examiner* — William Cheng
(74) *Attorney, Agent, or Firm* — Vierra Magen Marcus LLP

(57) ABSTRACT

A computer implemented method and apparatus can create an exposure regimen for a user. The regimen can be used to instruct an exposure device to expose the user to light at a wavelength, duration, and intensity, and over one or more days, which is sufficient to alter the user's circadian rhythm. The user may provide one or more preferences which allow the technology to create the exposure regimen sufficient to alter the user's circadian rhythm.

9 Claims, 5 Drawing Sheets

PROGRAMMABLE CIRCADIAN RHYTHM ADJUSTMENT

BACKGROUND

Sleep and wake behaviors are generated by an interaction of one's circadian rhythm, as well as social and environmental factors. A circadian rhythm is a self-sustaining biological activity oscillating with a periodicity near 24 hours. Circadian rhythms tend to move into phase synchrony with environmental rhythms, mainly the day/night cycle.

Light therapy has been shown to alter one's circadian rhythm. Therapy can be used to shift the biologic clock phase to facilitate sleep at a desired time of day/night. The biologic clock is, however, not equally amenable to phase shifts throughout its circadian period. Successful light therapy, requires the identification of circadian windows of opportunity for intervention.

Light therapy can yield phase advancement (positive shift), delay (negative shift), or be entirely phase neutral depending on the biologic clock time at which the light is administered. The biologic valence of light therapy is determined by 2 inherent features—wavelength and intensity. Visible light has an approximate wavelength spectrum of 380 (violet) to 760 (red) nm. It has been demonstrated that short wavelength blue light (~460 nm) possesses greater phase shifting properties than the rest of the visible light spectrum. The unit of intensity for visible light is lux. For example, the intensity of sunlight at midday measures over 100,000 lux.

SUMMARY

Technology is presented to adjust circadian rhythms to improve sleep. A method and apparatus can create an exposure regimen for a user. The regimen can be used to instruct an exposure device to expose the user to light at a wavelength, duration, and intensity, and over one or more days, which is sufficient to alter the user's circadian rhythm. The user may provide one or more preferences which allow the technology to create the exposure regimen sufficient to alter the user's circadian rhythm.

In one embodiment a computer implemented method of setting a circadian rhythm using a light exposure element is provided. A light exposure element is provided and the method receives a desired wake time. The method determines the determining an output intensity and light wavelength of the output element and calculates a regimen of exposure comprising a light duration, a light output intensity, and a frequency over a treatment period. The light exposure element is then activated to implement the regimen.

In another embodiment, an apparatus for setting circadian rhythms is provided. The apparatus includes a light exposure element capable of outputting light in a wavelength in a range of 380 to 760 nm. The apparatus may include a processing device including code for instructing the processing device to create a treatment regimen. The regimen includes an exposure duration, an exposure intensity, and an exposure treatment period. Also provided is code for controlling the light exposure element to selectively output light in a range of 380 to 760 nm for a calculated exposure duration, at a calculated intensity, and over the treatment period to alter the circadian rhythm.

This Summary is provided to introduce a selection of concepts in a simplified form that are further described below in the Detailed Description. This Summary is not intended to identify key features or essential features of the claimed subject matter, nor is it intended to be used as an aid in determining the scope of the claimed subject matter.

DETAILED DESCRIPTION

Technology is presented to enable an individual to adjust their own circadian rhythms to improve sleep. In one aspect, the technology is a computer implemented method which creates an exposure regimen for a user. The regimen can be used to instruct an exposure device to expose the user to light at a wavelength, duration, and intensity, and over one or more days, which is sufficient to alter the user's circadian rhythm. The user may provide one or more preferences which allow the technology to create the exposure regimen sufficient to alter the user's circadian rhythm.

In one aspect, a user inputs a target wake time at which the user would like to awaken from sleep and the technology provides an exposure regimen via an exposure device for one or more days to alter the user's wake time. In another element, the user provides a target wake up time, base time zone and travel time zone, and the technology provides an exposure regimen sufficient to reset the user's rhythm to the new time at the new time zone. In one aspect, the technology is enabled in a special purpose apparatus including a dedicated exposure element which provides light over a range of wavelengths and intensities. In another embodiment, any suitable processing device, including a general purpose computer or mobile processing device, which has the capability to drive a display, may implement the present technology.

The following technology is described by using flow diagrams to describe either the structure or the processing of certain embodiments to implement the systems and methods of the present technology. The technology, however, can also be used with any special purpose computer or other hardware system and all should be included within its scope.

Embodiments within the scope of the present technology also include articles of manufacture comprising program storage means having encoded therein program code. Such program storage can be any available media which can be accessed by a general purpose or special purpose computer. By way of example, and not limitation, such program storage means can comprise RAM, ROM, EEPROM, CD-ROM or other optical disk storage, magnetic disk storage or other magnetic storage devices, or any other medium which can be used to store the desired program code means and which can be accessed by a general purpose or special purpose computer. Combinations of the above should also be included within the scope of program storage. Program code comprises, for example, executable instructions and data which cause a general purpose computer or special purpose computer to perform a certain function or a group of functions.

Figure 1:
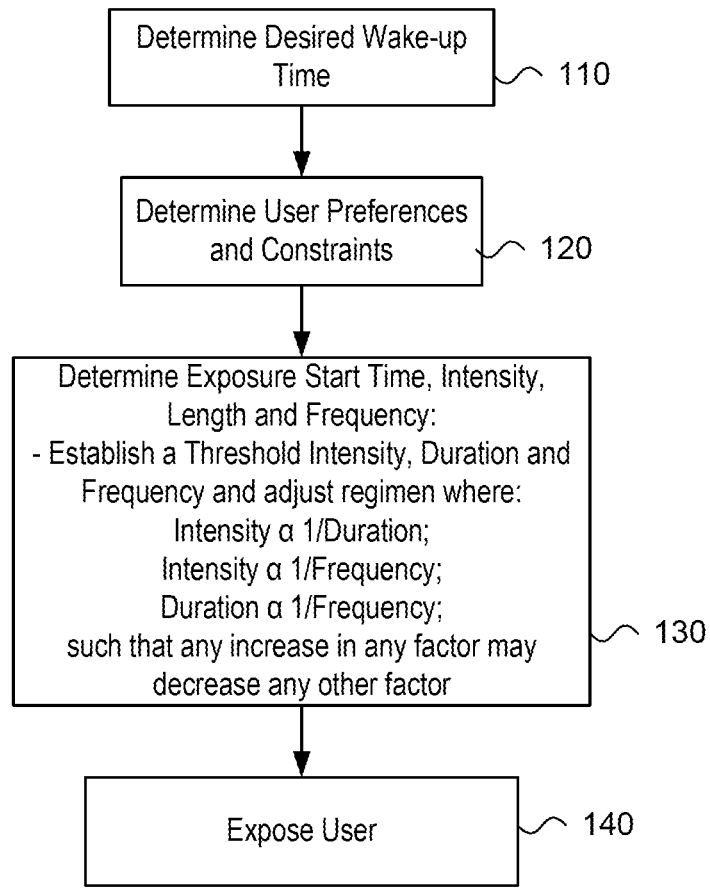
FIG. 1 depicts a first method in accordance with the present technology.

FIG. 1 illustrates a general method in accordance with the present technology which enables a user to adjust their circadian rhythms in order to improve the time at which they wake up or go to sleep. At step 110, a desired wake up time is determined. Determining a desired wake up time can occur in any number of ways. Where the technology is implemented in a special purpose device or in a general purpose processing device, an input interface may be provided allowing a user to simply input a new wake up time directly. Alternatively, a user can input a number of factors that will allow the technology to calculate a wake up time as discussed below with respect to FIG. 3. For example, if a user is going on a long trip and needs to adjust to a new time zone, the embodiment shown in FIG. 3 allows calculation of the desired wake up time based on a number of input factors. Any number of various user interfaces, both on a general purpose computing device, a mobile device, or a special purpose device (such as an alarm clock having an exposure element illustrated in FIG. 5) may accept the user input.

At step 120, user preferences and constraints are determined. In one embodiment, the user can simply enter a number of preferences and constraints via a user interface. Preferences and constraints can include factors such as how intense an exposure regimen is, how long the user wishes to be exposed, how many times the user wishes to be exposed (alternatively referred to herein as the frequency) and other factors. For example, a user may not wish to be exposed to a very intense light, but might prefer being exposed to a less intense light for a longer period of time. Alternatively, the user may wish to be exposed for shorter periods of time at higher intensity light.

Constraints may also include items such as intensity and light wavelength. Certain types of devices in which the present technology is utilized may have limitations on the amount of intensity which the device can provide. In one embodiment, the technology can be implemented in a standard mobile device using the mobile device's screen. In such embodiments, limitations may be present on the amount of intensity and the wavelengths that the device is capable of outputting to the user.

Once the preferences and constraints are determined at step 120, a regimen is calculated at step 130. The regimen includes determining an exposure start time, an exposure intensity, an exposure length, and a frequency of exposures. The frequency may occur over a number of days or cycles within a given day. The regimen is calculated by establishing a threshold intensity duration and frequency and adjusting each of the intensity duration and frequency based on an inversely proportional relationship between the factors. Thus, increasing the duration of the exposure may decrease the frequency or intensity. Likewise, decreasing the intensity might increase the duration or frequency. Any increase in any factor may decrease any other factor or multiple factors, and any decrease in any factor may increase any other factor or multiple factors. Multiple regimens may be calculated based on both user preferences and device constraints. In one embodiment, where a user provides no preferences, optimal selections will be created. The optimal regimens will be calculated based on one or more preferences set by a programmer implementing the method shown in FIG. 1.

Once an exposure regimen is calculated at step 130, the user is exposed at step 140 at the intensity, start time, for the calculated length, and over a number of cycles as specified in the regimen. It should be noted that the start time, intensity, length, and frequency may be varied within the cycle. That is, on one day, an intensity may be higher or lower than on a second day within the cycle. Likewise, the exposure time may be longer or shorter in various cycles.

Figure 2:
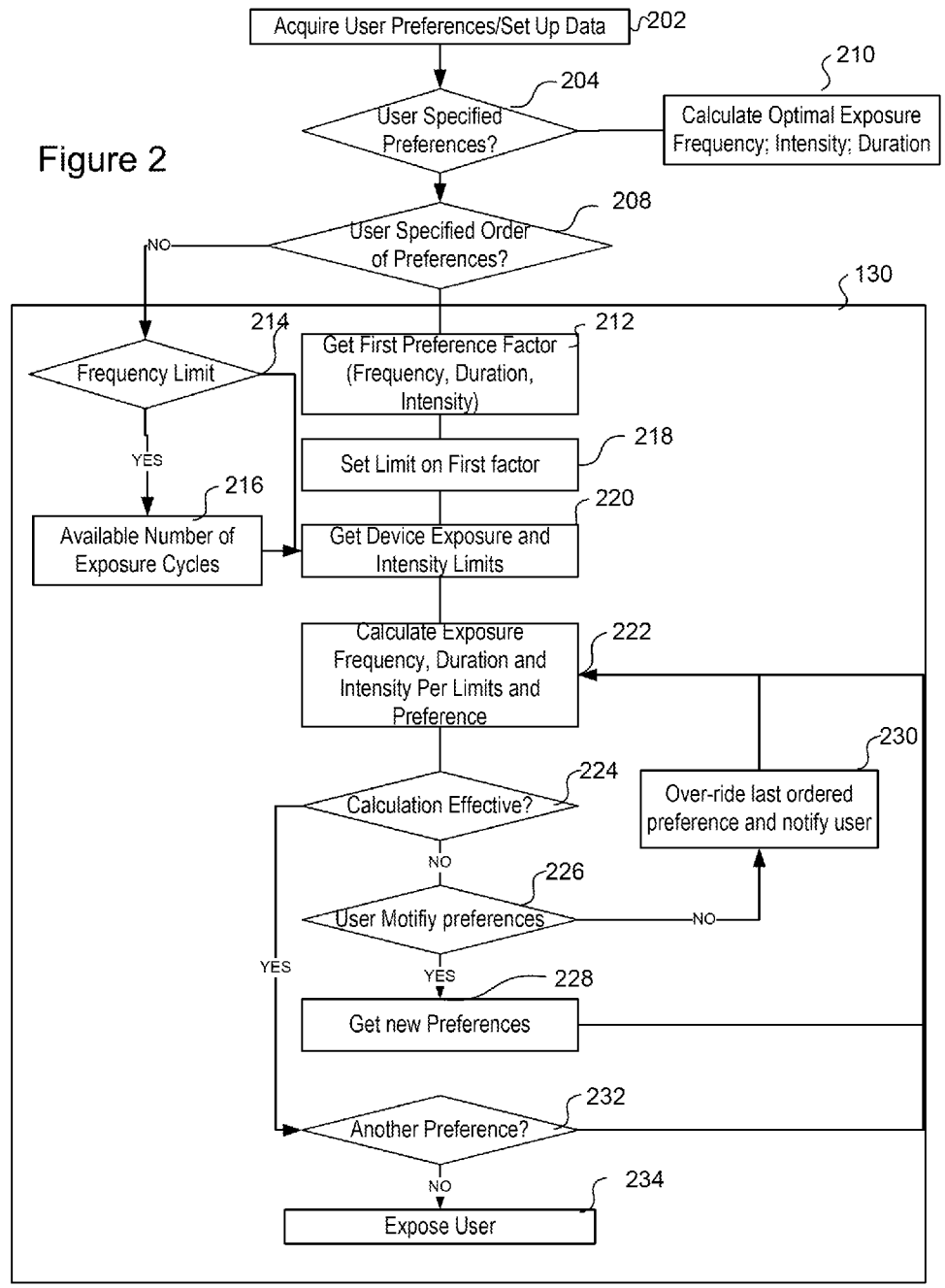
FIG. 2 depicts a method of determining user preferences.

FIG. 2 illustrates a more detailed flow chart illustrating the method of FIG. 1. Steps 120 and 130 are illustrated in FIG. 2. Step 120 may involve acquiring user preferences and set up data at 202. As noted above this can include providing a user interface which allows a user to input one or more preferences. For example, the user may be invited to provide the desired start time or wake up time, or limit the intensity or frequency of the exposures. In one example, if a user is traveling in a limited number of days before beginning the exposure, the user may input this number of days so that the system optimizes the exposure based on the limited frequency period available. It should be recognized that the frequency adjustment may occur both before and after the user travels, in this example.

At step 204, determination is made as to whether or not the user has in fact specified preferences. If the user has not specified any preferences, then the regimen is calculated at 210 by calculating an optimal exposure intensity, frequency and duration based on device constraints. If the user has specified preferences, then at 208 a determination is made as to whether or not the user has specified a specific order of preferences. For example, a user may be prompted to provide a preference over whether or not the user wishes to limit the intensity of the light more than the user wishes to limit the frequency of exposure. In such cases, and where possible, the technology will take into account the user's preferences with respect to the calculation, and may notify the user if the preferences conflict with the availability of providing an effective regimen which would alter the circadian rhythm. If the user does not specify an order of preferences, then the system will check to see whether a frequency limit is in place at 214. A frequency limit would be a limit on the number of exposure cycles that are provided as indicated at 216. A frequency limit may have the effect of increasing device exposure and intensity requirements in the regimen.

If the user has specified an order of preferences at 208, then at 212, the first preference factor specified is retrieved and a limit set in the first preference factor at 218. Device exposure and intensity constraints are retrieved at 220. As noted above, the technology can occur in any number of different devices and as such may be operating in a processing device having an exposure screen with limited intensity or wavelength availability. Once the device exposure and intensity limits are retrieved, the exposure frequency duration and intensity are calculated based on the known limits and any preference which has been retrieved at 222. Once this calculation occurs, a determination is made at 224 as to whether or not such regimen would be effective. The determination of whether or not the regimen would be effective can be based on whether or not certain thresholds for intensity, duration and infrequency are met, given the known starting time of the device. If it is determined that the calculation is effective, then a check for other preferences is made at 232 and the calculation can be repeated to determine if it can be further limited by returning to step 222.

If the calculation is not effective at 224, then the user can be prompted at 226 as to whether or not the user wishes to modify the preferences previously set. If the user does wish to modify the preferences, then the new preferences will be retrieved at 228 and the regimen recalculated at 222. If the user does not wish to modify the preferences, then the system will notify the user that the regimen is not likely to be effective, and provide an option to override the last order preference at 230. In one embodiment, the technology may provide both user preferred regimens known not to be effective, and allow the user to select the potentially ineffective regimens, as well as optimized regimens which are likely to be effective, and allow the user to choose those. In another embodiment, the user will not be provided with ineffective regimens, the user preferences can be overridden and the user notified that preferences have been overridden in order to allow the user to solely select an option which will provide a reset of the user's circadian rhythm.

Figure 3:
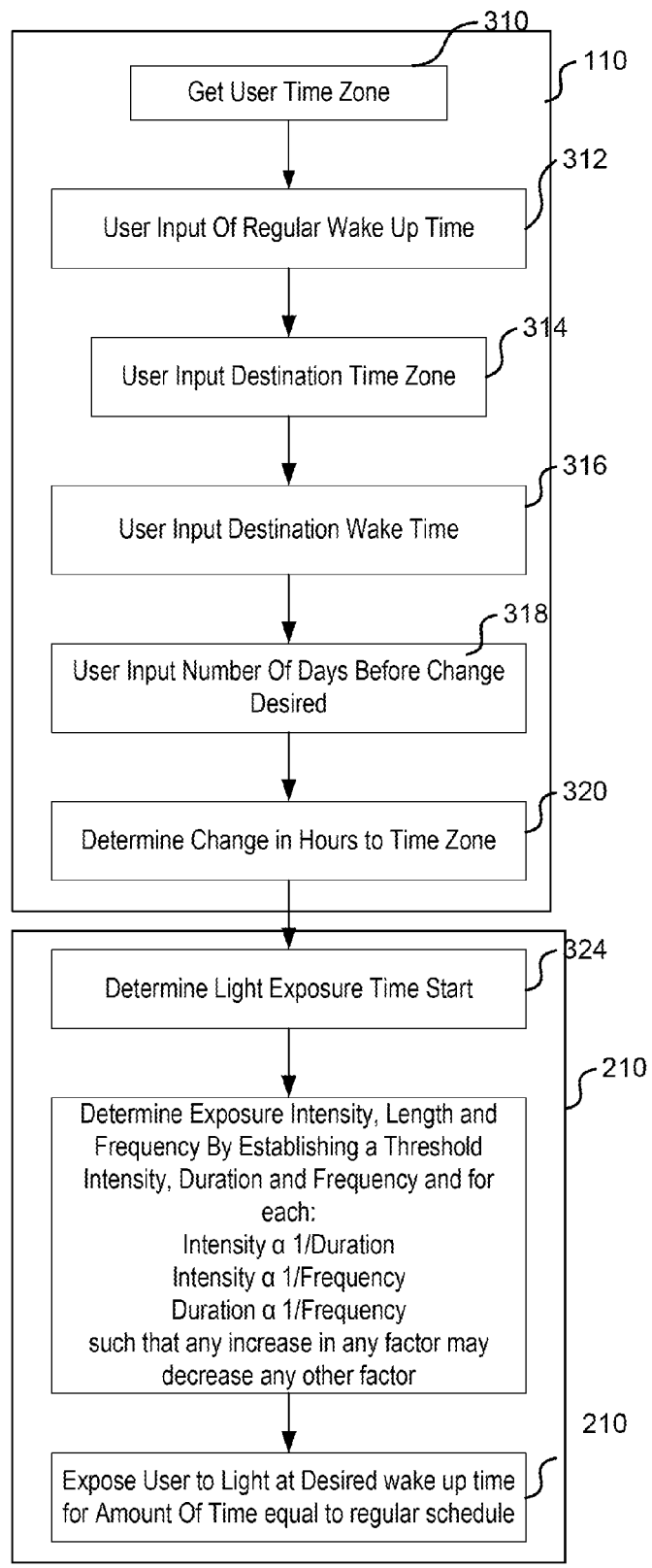
FIG. 3 is an alternative method for performing the present technology.
Figure 4:
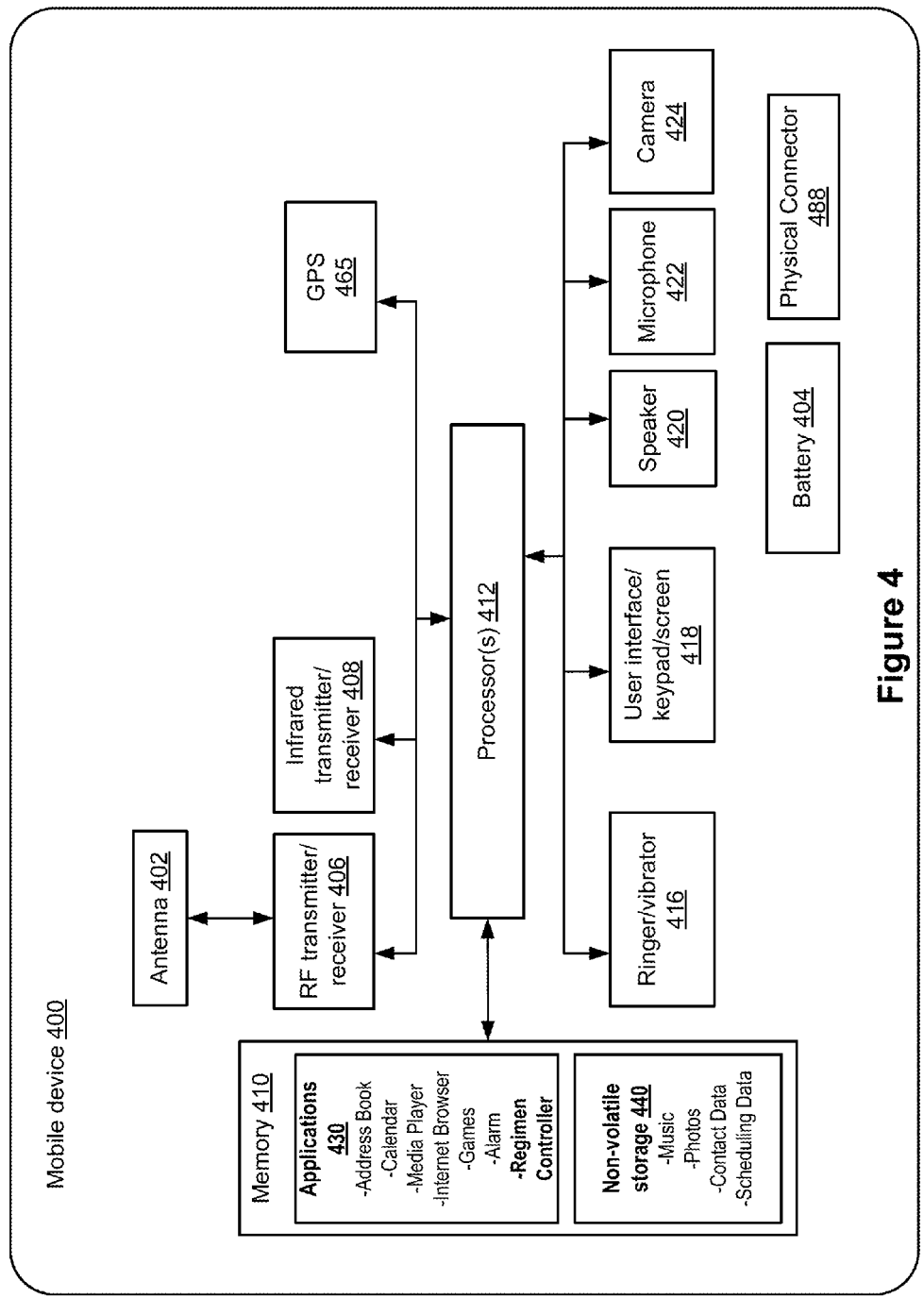
FIG. 4 is a processing device suitable for use in the present technology.
Figure 5:
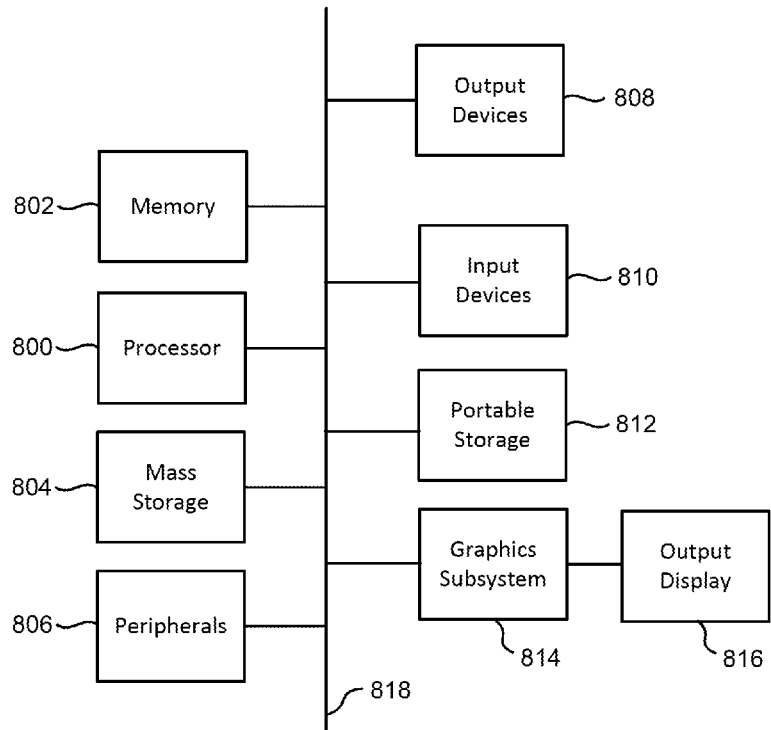
FIG. 5 is a representation of a consumer device suitable for implementing the present technology.
Figure 6:
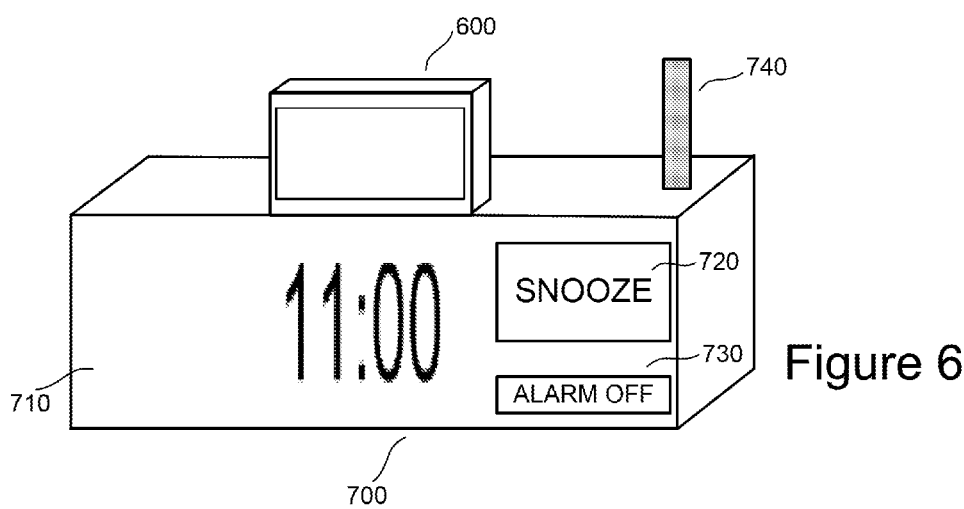
FIG. 6 is an alternative representation of a processing device suitable for implementing the present technology.

The methods presented in FIGS. 1 through 3 may be incorporated into a hardware device as illustrated in FIGS. 4 through 6. In alternate embodiments, the methods illustrated in FIGS. 1 through 3 are performed by one or more processing devices in the hardware apparatus under the control of instructions for implementing the processes illustrated in FIGS. 1 through 3.

FIG. 3 illustrates an alternative embodiment for providing user input in case where the user is planning to travel for a great distance. At step 310, the user time zone is retrieved. The user time zone can be retrieved by a direct user input of the time zone or by calculating known global positioning system coordinates which the user is located. Alternatively, a system clock may be read having known time zone coordinates. At step 312, the user may be prompted to input the user's regular wake up time. For example, a user can be prompted to input the time that the user normally awakes within the known time zone required at step 310. At step 314, the user's destination time zone is input by the user at 314. In addition, the user's destination wake up time can be input at 316. At 318, the user can be prompted to input the number of days before the change in wake up time is desired. At 320, the method calculates the change in the number of hours to the time zone, and determines the light exposure start time at 324. A light exposure start time can be calculated by once the light exposure time is calculated at 324, then the intensity, length and frequency are calculated at 326. In this instance, the light exposure time is fixed.

The light exposure time can be calculated by adding the change to the user's regular schedule to the desired wake up time. The change to the user's regular schedule is calculated by determining the difference between the regular wake up time and the desired wake up time and adding the change to the new time zone. The light exposure time will be the change in hours to the new time zone added to the desired wake up time. At step 330, the user is exposed to light at the desired wake up time for an amount of time equal to the regimen. In order to calculate wake up time, if the regular wake up time=A1, the desired wake up time=A2, and the change to a new time zone=B, then the change to one's regular schedule is $\{A1-A2\}+B=C$ and the light exposure start time will be=A2+C. Note that exposure times can be provided both before and after one travels.

Taking the below example where one is flying east to west, from San Francisco to Tokyo:
  Regular wake up time=8 am PST (a1)
  Desired Wake Up Time=1 am PST (a2)
  Time Zone Delta=−8 hours (b)
  Delta to Schedule=7+(−8)=1
  Exposure time=2 am PST In the above example, a user might input their normal wake time, desired wake time and respective time zones in order for the system to create the necessary calculation of start time and regimen.

FIG. 4 illustrates an exemplary mobile device suitable for use in the present technology. FIG. 4 is a block diagram of one embodiment of a mobile device 400. Mobile devices may include laptop computers, pocket computers, mobile phones, personal digital assistants, and handheld media devices that have been integrated with wireless receiver/transmitter technology.

Mobile device 400 includes one or more processors 412 and memory 410. Memory 410 includes applications 430 and non-volatile storage 440. Memory 410 can be any variety of memory storage media types, including non-volatile and volatile memory. A mobile device operating system handles the different operations of the mobile device 400 and may contain user interfaces for operations, such as placing and receiving phone calls, text messaging, checking voicemail, and the like. The applications 430 can be any assortment of programs, such as a camera application for photos and/or videos, an address book, a calendar application, a media player, an internet browser, games, an alarm application, and other applications, including, for example, a Regimen Controller application comprising code for instructing the processor 412 to perform the above methods. The non-volatile storage component 440 in memory 410 may contain data such as music, photos, contact data, scheduling data, and other files.

The one or more processors 412 also communicates with RF transmitter/receiver 406 which in turn is coupled to an antenna 402, with infrared transmitter/receiver 408, with global positioning service (GPS) receiver 465, and with movement/orientation sensor 414 which may include an accelerometer and/or magnetometer. RF transmitter/receiver 408 may enable wireless communication via various wireless technology standards such as Bluetooth or the IEEE 802.11 standards. Accelerometers have been incorporated into mobile devices to enable applications such as intelligent user interface applications that let users input commands through gestures, and orientation applications which can automatically change the display from portrait to landscape when the mobile device is rotated. An accelerometer can be provided, e.g., by a micro-electromechanical system (MEMS) which is a tiny mechanical device (of micrometer dimensions) built onto a semiconductor chip. Acceleration direction, as well as orientation, vibration, and shock can be sensed. The one or more processors 412 further communicate with a ringer/vibrator 416, a user interface keypad/screen 418, a speaker 420, a microphone 422, a camera 424, a light sensor 426, and a temperature sensor 428. The user interface keypad/screen may include a touch-sensitive screen display.

The one or more processors 412 controls transmission and reception of wireless signals. During a transmission mode, the one or more processors 412 provide voice signals from microphone 422, or other data signals, to the RF transmitter/receiver 406. The transmitter/receiver 406 transmits the signals through the antenna 402. The ringer/vibrator 416 is used to signal an incoming call, text message, calendar reminder, alarm clock reminder, or other notification to the user. During a receiving mode, the RF transmitter/receiver 406 receives a voice signal or data signal from a remote station through the antenna 402. A received voice signal is provided to the speaker 420 while other received data signals are processed appropriately.

Additionally, a physical connector 488 may be used to connect the mobile device 400 to an external power source, such as an AC adapter or powered docking station, in order to recharge battery 404. The physical connector 488 may also be used as a data connection to an external computing device. The data connection allows for operations such as synchronizing mobile device data with the computing data on another device.

FIG. 5 illustrates a high level block diagram of a computer system that can be used to implement the present technology. The computer system in FIG. 5 includes processor unit 800 and main memory 802. Processor unit 800 may contain a single microprocessor, or may contain a plurality of microprocessors for configuring the computer system as a multi-processor system. Main memory 802 stores, in part, instructions and data for execution by processor unit 800. If the system of the present technology is wholly or partially implemented in software, main memory 802 can store the executable code when in operation. Main memory 802 may include banks of dynamic random access memory (DRAM) as well as high speed cache memory.

The system of FIG. 5 further includes mass storage device 804, peripheral device(s) 806, user input device(s) 810, portable storage medium drive(s) 812, graphics subsystem 814, and output display 816. For purposes of simplicity, the components shown in FIG. 19 are depicted as being connected via a single bus 818. However, the components may be connected through one or more data transport means. For example, processor unit 800 and main memory 802 may be connected via a local microprocessor bus, and the mass storage device 804, peripheral device(s) 806, portable storage medium drive(s) 812, and graphics subsystem 814 may be connected via one or more input/output (I/O) buses. Mass storage device 804, which may be implemented with a magnetic disk drive or an optical disk drive, is a non volatile storage device for storing data and instructions for use by processor unit 800. In one embodiment, mass storage device 804 stores the system software for implementing the present technology for purposes of loading to main memory 802.

Portable storage medium drive 812 operates in conjunction with a portable non volatile storage medium, such as a floppy disk, to input and output data and code to and from the computer system of FIG. 19. In one embodiment, the system software for implementing the present technology is stored on such a portable medium, and is input to the computer system via the portable storage medium drive 812. Peripheral device(s) 806 may include any type of computer support device, such as an input/output (I/O) interface, to add additional functionality to the computer system. For example, peripheral device(s) 806 may include a network interface for connecting the computer system to a network, a modem, a router, etc.

User input device(s) 810 provide a portion of a user interface. User input device(s) 810 may include an alpha-numeric keypad for inputting alpha-numeric and other information, or a pointing device, such as a mouse, a trackball, stylus, or cursor direction keys. In order to display textual and graphical information, the computer system of FIG. 19 includes graphics subsystem 814 and output display 816. Output display 816 may include a cathode ray tube (CRT) display, liquid crystal display (LCD) or other suitable display device. Graphics subsystem 814 receives textual and graphical information, and processes the information for output to display 816. Additionally, the system of FIG. 28 includes output devices 808. Examples of suitable output devices include speakers, printers, network interfaces, monitors, etc.

The components contained in the computer system of FIG. 19 are those typically found in computer systems suitable for use with the present technology, and are intended to represent a broad category of such computer components that are well known in the art. Thus, the computer system of FIG. 19 can be a personal computer, handheld computing device, Internet-enabled telephone, workstation, server, minicomputer, mainframe computer, or any other computing device. The computer can also include different bus configurations, networked platforms, multi-processor platforms, etc. Various operating systems can be used including Unix, Linux, Windows, Macintosh OS, Palm OS, and other suitable operating systems.

FIG. 6 is a perspective view of an exemplary special purpose device 700 which may comprise, for example, an alarm clock. The alarm clock 700 can include a front display 710 and an exposure device 600 which outputs light at various frequencies in accordance with the discussion herein. The alarm clock may have various standard features such as an alarm, snooze button 720, off switch 730, and antenna, and may include any of the components of the mobile device of FIG. 4 or general purpose computer of FIG. 5. In one embodiment, the exposure device 600 outputs light in a wavelength in a range of about 380 to 760 nanometers, and in a further embodiment, the output of the exposure device is approximately that of short wavelength blue light (approximately 460 nanometers) the output of the device may comprise an intensity in the range of zero to 12,000 lux, in one embodiment the output range will be about 50 to 550 lux.

Although the subject matter has been described in language specific to structural features and/or methodological acts, it is to be understood that the subject matter defined in the appended claims is not necessarily limited to the specific features or acts described above. Rather, the specific features and acts described above are disclosed as example forms of implementing the claims.

What is claimed is:

1. An apparatus for resetting circadian rhythms, comprising:
a light exposure element capable of outputting light in a wavelength in a range of 380 to 760 nm;
a processing device including code for instructing the processing device to receive ordered user preferences as inputs to a treatment regimen from a user and calculate the treatment regimen responsive to the ordered user preferences received, the treatment regimen including at least an exposure duration, an exposure intensity and a regimen treatment period, the device capable of receiving as inputs to calculate the treatment regimen ordered user preferences for each of the exposure duration, the exposure intensity, and the regimen treatment period, and code for controlling the light exposure element to selectively output light in a range of 380 to 760 nm for the exposure duration, at the exposure intensity, and over the regimen treatment period calculated in the treatment regimen, the exposure duration, exposure intensity and regimen treatment period calculated in the treatment regimen being selected first from one or more input ordered preferences received to alter the circadian rhythm of the user.

2. The apparatus of claim 1 wherein the processing device includes code directing the exposure element to output light at a wavelength of approximately 460 nm.

3. The apparatus of claim 1 further including a user input device capable of receiving user preferences on at least one of intensity, duration and frequency.

4. The apparatus of claim 3 wherein device is configured to receive as the input user preferences includes an input of a limitation on at least one of intensity, duration and frequency.

5. The apparatus of claim 1 wherein the regimen is calculated by adjusting one of the intensity, frequency, or duration in an inverse proportion to an increase in at least one other of the intensity, frequency period or duration.

6. The apparatus of claim 1 further including code determining intensity and wavelength output limitations of the exposure element, and the treatment regimen is calculated to compensate for said limitations.

7. The apparatus of claim 1 wherein the apparatus is a mobile device and the exposure element is a display screen of the mobile device.

8. The apparatus of claim 1 wherein the apparatus is a general purpose computing device and the exposure element is a computer monitor.

9. An apparatus for resetting circadian rhythms, comprising:
   a light exposure element capable of outputting light in a wavelength in a range of 380 to 760 nm;
   a processing device including code for instructing the processing device to receive ordered user preferences as inputs to a treatment regimen from a user and calculate the treatment regimen responsive to the ordered user preferences received, the treatment regimen including at least a exposure duration, a exposure intensity and a regimen treatment period, the device capable of receiving as inputs to calculate the treatment regimen ordered preferences for each of the exposure duration, the exposure intensity, and the regimen treatment period, and code for controlling the light exposure element to selectively output light in a range of 380 to 760 nm for the exposure duration, at the exposure intensity, and over the regimen treatment period for the treatment regimen calculated, the exposure duration, exposure intensity and regimen treatment period in the treatment regimen calculated being selected first from the one or more ordered preferences received, and if no preference is received for the exposure duration then using a calculated exposure duration, if no preference is received for the exposure intensity then using a calculated exposure intensity, and if no preference is received for the regimen treatment period then using a calculated regimen treatment period for the treatment regimen to alter the circadian rhythm of the user.

* * * * *